United States Patent [19]

Schmidt

[11] 4,064,242

[45] Dec. 20, 1977

[54] 7-ACYLAMINO-3-[1-(2,3-DIHYDROXY-PROPYL)TETRAZOLE-5-YLTHIOMETHYL]-3-CEPHEM-4-CARBOXYLIC ACIDS

[75] Inventor: Stanley J. Schmidt, Ardmore, Pa.

[73] Assignee: SmithKline Corporation, Philadelphia, Pa.

[21] Appl. No.: 738,774

[22] Filed: Nov. 4, 1976

[51] Int. Cl.$^2$ .................. A61K 31/345; C07D 501/36
[52] U.S. Cl. ........................................ 424/246; 544/26
[58] Field of Search ..................... 260/243 C; 424/246

[56] References Cited

U.S. PATENT DOCUMENTS 3,993,758   11/1976   Burton et al. ..................... 260/243 C

FOREIGN PATENT DOCUMENTS 2,415,402   10/1974   Germany.

*Primary Examiner*—Nicholas S. Rizzo
*Attorney, Agent, or Firm*—William H. Edgerton

[57] ABSTRACT

New semisynthetic cephalosporins characterized by having structures with a 1-dihydroxypropyltetrazole-5-ylthiomethyl group at position 3. Exemplary is the antibacterially effective 7-D-mandelamido-3-[1-(2,3-dihyroxypropyl)tetrazole-5-ylthiomethyl]-3-cephem-4-carboxylic and 7-(D-α-phenyl-α-aminoacetamindo)-3-[1-(2,3-dihydroxypropyl)-tetrazole-5-ylthiomethyl]-3-cephem-4-carboxylic acid.

6 Claims, No Drawings

7-ACYLAMINO-3-[1-(2,3-DIHYDROXYPROPYL)-TETRAZOLE-5-YLTHIOMETHYL]-3-CEPHEM-4-CARBOXYLIC ACIDS

This invention relates to a new series of cephalosporin compounds having antibacterial activity and to intermediates useful for preparing them. The stuctures of the new compounds are characterized by having at the 3-position a dihydroxypropyl substituted tetrazole group.

To the best of my knowledge the compounds described herein are novel. A number of disclosures such as Takeda, Belgian Pat. No. 823,861 disclose monohydroxyalkyltetrazole substituted cephalosporins very broadly but not specifically. A coworker has filed an as yet unpublished application Ser. No. 609,333 filed on Sept. 2, 1975 on the monohydroxy compounds. Nowhere are dihydroxypropyltetrazole containing cephalosporins disclosed. Also they can not be prepared by the methods disclosed for the monohydroxyalkyl compounds in the Ser. No. 609,333 application. They additionally are exceptionally water soluble compared with the methyl or monohydroxypropyl congeners.

Exemplary of the compounds of this invention are those represented by the following structural formula:

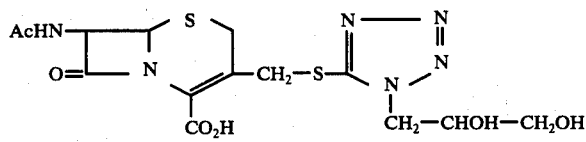

Formula I in which Ac represents a pharmaceutically acceptable acyl group known to be of utility as a substituent on the 7-amino group in the structures of known or prior art cephalosporins or on the 6-amino group in the structures of known or prior art penicillins. Representative acyl substituents are:

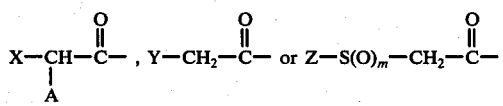

wherein:
X is thienyl, furyl, phenyl or phenyl monosubstituted with hydroxy, hydroxymethyl, formamido or ureido;
A is $NH_2$, OH, COOH, $SO_3H$, formyloxy or, when the α-C-hydrogen is absent, methoxyimino;
Y is cyano, sydnone, pyridone, thienyl, o-aminomethylphenyl, phenyl or tetrazolyl;
Z is methyl, trifluoromethyl, trifluoroethyl, pyridyl or cyanomethyl; and
m is 0 to 2.

Each of the three partial structures above represent subgeneric groups of compounds covered by this invention.

Representative 7-acylamino substituents of the compounds of formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
syn-2-methoxyimino-2-α-furylacetamido
4pyridylthioacetamido
o-aminomethylphenylacetamido Others together with N-acylation procedures may be found in Cephalosporins and Penicillins, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula I from which they derive utility: the salts, as stated above easily split ester or ether derivatives of either a carboxy or hydroxy function, amide derivatives at an amino radical such as in a 7-glycylamino group as the furyl-, pyranyl-, oxolanyl- or oxiranyl-carbonyl amides (i.e. Belgian Pat. No. 835,295), the solvates such as hydrates, glycolates or alcoholates. As examples of these, one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or phenyl glycyl substituents at 7. The D-forms of these subgeneric groups are preferred. Also an assymetric center is present at the second carbon on the novel dihydroxypropyl substituted on the 3-5-tetrazole moiety. This of course can also lead to optical isomers which can be separated by prior art methods usually on the thiol but to no particular advantage over the natural mixtures.

The compounds of this invention are most conveniently prepared by a displacement of the acetoxy group of a known 7-acylaminocephalosporanic acid (II) by 1-(2,3-dihydroxypropyl)-tetrazole-5-thiol (III) usually as the sodium or other alkali metal salt. Alternatively a similar displacement with the thiol can be run on 7-aminocephalosporanic acid to give 7-amino-3-[1-(2,3-dihydroxypropyl)tetrazole-5-ylthiomethyl]-3-cephem-4-carboxylic acid (IV) which may then be N-acylated as known to the art as described above. Suitable protective groups may be used in either method as is known to the art (see "Protective Groups in Organic Chemistry", J.F.W. McOmie, Plenum Press, 1973, Chapter 2 and 3 for use of amino, carboxy, sulfo or hydroxyl protective groups).

For example, the t-butyl (for COOH) or t-butoxycarbonyl (for $NH_2$) groups are easily removed by treatment with trifluoroacetic acid.

The compounds of Formula I have antibacterial activity against either Gram positive or Gram negative bacteria with minimum inhibitory concentrations (MIC's) in vitro from 0.4 to 200 ug/ml. Test results for 7-D-mandel-amido-3-[1-(2,3-dihydroxypropyl]tetrazole-5-ylthiomethyl)-3-cephem-4-carboxylic acid, tetrahydrate (A) and 7-(D-α-phenyl-α-aminoacetamido)-3-[1-(2,3-dihydroxypropyl)tetrazole-5-yl-thiomethyl]-3-cephem-4-carboxylic acid hydrate (B) are:

containing cephalosporins of this invention is an advantage for preparing injectable preparations.

The compounds of Formula I are formulated and administered in the same manner as other prior art cephalosporins such as cephazolin or cephalothin. The dosage regimen comprises administration, preferably by injection, of an active but nontoxic quantity of a compound of Formula I selected from the dosage unit range of from about 250 mg to 600 mg with the total daily dosage regimen being from about 750 mg to 6g. The compounds as their sodium or potassium salts are very water soluble compared with non-hydroxy congeners in the art. The precise dosages are dependent upon the age and weight of the subject and on the susceptibility of the infection being treated to each individual. These can be determined by those skilled in the art based on the data disclosed herein compared with that available to the art attained with the known cephalosporins outlined herebefore.

The following examples illustrate the invention but are not to be construed as limiting the scope thereof. Temperatures are in degrees Centigrade (° C.) unless otherwise stated.

EXAMPLE 1

A mixture of 85 g (0.936 mol) of 3-amino-1,2-propanediol (85%), 130 ml (0.936 mol) of triethylamine and 500 ml of ethanol is stirred and cooled in an ice bath while 71 g (0.936 mol) of carbon disulfide is added.

|  | A | B | Cefazolin | | Cephalothin | |
|---|---|---|---|---|---|---|
| S. aureus HH 127 | 1.6 | 12.5 | 0.4 | (0.4) | 0.2 | (0.4) |
| S. aureus SK 23390 | 0.8 | 6.3 | 0.2 | (0.2) | 0.2 | (0.2) |
| S. aureus villaluz SK 70390 | >50 | 50 | 200 | (100) | 100 | (50) |
| Strep. Faecalis HH 34358 | 25 | 50 | 6.3 | (6.3) | 12.5 | (12.5) |
| E. coli SK 12140 | 0.8 | 6.3 | 1.6 | (1.6) | 3.1 | (3.1) |
| E. coli HH 33779 | 1.6 | 3.1 | 1.6 | (1.6) | 6.3 | (6.3) |
| Kleb. pneumo. SK 4200 | 0.8 | 3.1 | 1.6 | (1.6) | 1.6 | (3.1) |
| Kleb. pneumo. SK 1200 | 0.4 | 3.1 | 0.8 | (0.8) | 1.6 | (1.6) |
| Salmonella ATCC 12176 | 0.4 | 0.8 | 0.8 | (0.8) | 0.8 | (0.8) |
| Pseudo. aeru. HH 63 | >200 | >200 | >200 | (>200) | >200 | (>200) |
| Serratia marc. ATCC 13880 | 6.3 | 12.5 | >200 | (>200) | >200 | (>200) |
| Proteus morgani 179 | 1.6 | 6.3 | 200 | (100) | >200 | (>200) |
| Entero. aerog. ATCC 13048 | 1.6 | 6.3 | 1.6 | (1.6) | 12.5 | (12.5) |
| Entero. cloacae HH 31254 | 0.8 | 1.6 | 0.8 | (0.8) | 6.3 | (6.3) |
| Proteus mirabilis PN-444 | 0.8 | 6.3 | 3.1 | (3.1) | 3.1 | (3.1) |

Compound A gave an $ED_{50}$ in mice of 1.56 mg/kg (s.c.) and 25 mg/kg (p.o.) against *E. coli*. Cephalexin gives comparable values of 15.7 (s.c.) and 21 (p.o.) against E. coli. Compound A gave an $ED_{50}$ in mice of 1.82 (1.34) (s.c.) and 35 (19) (p.o.) against *Kleb. pneumo.* Cephalexin was 18 and 21.5. Cephaloridine 6.25 and 15.6. This data is representative of the results obtained and not exhaustive since other tests have been carried out.

Pharmaceutical compositions having antibacterial activity which comprise a pharmaceutical carrier containing an active but nontoxic quantity of a compound of Formula I as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration. The high water solubility of the dihydroxypropyltetrazole After stirring at room temperature for 1½ hours, 300 ml of water is added followed by cooling the mixture and adding thereto 133 g (0.936 mol) of methyliodide. The mixture was stirred over the weekend.

The mixture was evaporated to give a syrup which was taken up in 200 ml of brine. The mixture was acidified to pH 3 with hydrochloric acid then extracted with ethyl acetate to give the desired methyldithiocarbamate. The triethylamine salt was separated by chloroform extraction.

The crude dried dithiocarbamate (6.5 g) was dissolved in 150 ml of dry dimethylformamide with 0.03 g of p-toluene sulfonic acid. Evaporated off 75 ml of solvent. An excess of 2,2-dimethoxypropane is added and the methanol azeotrope was distilled off the reaction mixture until the reaction was complete. The residue from the distillation was made basic with sodium bicarbonate then extracted with ether to produce the desired acetonide after washing, drying and evaporation.

The blocked dihydroxythiocarbamate (6.6 g) was reacted with 1.6 g of sodium azide in water for ½ hour at reflux. The mixture was evaporated in vacuo to give a residue which was extracted with ethyl acetate. The extracts were evaporated to give the crude tetrazole which was deblocked by reacting with an excess of trifluoroacetic acid. The mixture was evaporated to give a solid which was dissolved in ethyl acetate. After washing the organic extracts with brine and drying, the extracts were reacted with sodium 2-ethylhexanoate to form the solid sodium salt of 1-(2,3-dihydroxypropyl)-tetrazole-5-thiol hydrate. N.M.R. consistant.

Anal. Calc: C, 24.24; H, 3.56; N, 28.29. Found: C, 22.30; H, 4.06; N, 25.87 C, 22.22; H, 4.20; N, 25.91.

Alternatively the extracts of the TFA reaction may be evaporated to form the free thiol. Other salts thereof can be made such as the potassium or calcium salts.

EXAMPLE 2

A mixture of 3 g of 7-D-(—-mandelamidocephalosporanic acid and 0.9 g of the thiol salt from Example 1 in 50 ml of water at pH of 7 was heated at 65° for 2 hours. Thin layer analysis showed the reaction was complete. The mixture was taken to pH of 3.5 with sulfuric acid and extracted with ethyl acetate. The water layers were evaporated and the residue taken up in ethanol. Again the filtered ethanol extracts were evaporated. The residue was taken up in a minimum amount of water and absolute ethanol added until the solution was cloudy. Cooling separated a solid. The ethanol soluble material was the desired product, 7-D-mandelamido-3-[1-(2,3-dihydroxy)propyl]tetrazole-5-yl-thiomethyl-3-cephem-4-carboxylic acid tetrahydrate, m.p. 110°–111°.

The material can be optionally purified further over an XAD-4 resin with ethanol elution.

Anal. Calc: C, 40.40; H, 5.09; N, 14.13.
Found: C, 40.50; H, 4.76; N. 13.73.

EXAMPLE 3

A mixture of 2 g of 7-(D-α-t-butoxycarbonylaminophenylacetamido)cephalosporanic acid and 0.78 g of the thiol salt from Example 2 in 50 ml of water was reacted at 68° for 3 hours. Analysis of the reaction mixture indicated the reaction was not complete so heating was continued 1½ hours longer.

The cooled reaction mixture was extracted with ethyl acetate. The aqueous layers were taken to pH 3 and extracted again. Evaporation of this dried extract gave 1 g of the desired 7-(D-α-phenyl-α-aminoacetamido)-3-[1-(2,3-dihydroxy-propyl)tetrazole-5-yl-thiomethyl]-3-cephem-4-carboxylic acid as the t-boc derivative.

The product may be purified further by passing over silica with elution by chloroform-isopropanol-formic acid. The t-boc derivative was reacted with trifluoroacetic acid-anisole at room temperature. Evaporation and ethyl acetate wash give the desired deblocked product as the 2 ¾ hydrate, m.p. 110°–113°.

Anal. Calc: C, 43.26; H, 4.93; N, 16.81.
Found: C, 43.13; H, 4.60; N, 16.70.

Similar treatment of 7-(D-α-t-butoxycarbonylamino-4-hydroxyphenylacetamido)cephalosporanic acid gives 7-(D-α-p-hydroxyphenyl-α-aminoacetamido-[1-(2,3-dihydroxypropyl)-tetrazole-5-yl-thiomethyl]-3-cephem-4-carboxylic acid as a hydrate.

EXAMPLE 4

A mixture of 12.2 mmol of 2,3-dihydroxypropyl-tetrazolethiol (obtained from the salt by neutralization in water/organic solvent mixture) with a stoichiometric quantity of sodium bicarbonate and 7-trifluoromethylthioacetamido-cephalosporanic acid in 50 ml of water is stirred at 70° for 5 hours. The reaction mixture is cooled and worked up as described above to give 7-trifluoromethylthioacetamido-3-[1-(2,3-dihydroxypropyl)tetrazole-5-ylthiomethyl]-3-cephem-4-carboxylic acid sodium salt. Substituting 7-(2-thienylacetamidocephalosporanic acid gives 7-(2-thienylacetamido)-3-[-1-(2,3-dihydroxypropyl)tetrazole-5-ylthiomethyl]-3-cephem-4-carboxylic acid sodium salt.

Stoichiometric quantities of cephalosporanic acids having the individual 7-acylamino substituent listed hereabove may be substituted in Examples 1–3 with variations which will be obvious to those skilled in this art.

EXAMPLE 5

An injectable pharmaceutical composition is formed by adding sterile saline solution (2 ml) to 500 mg of the product of Example 2. This material is injected parenterally four times daily to a human patient infected with susceptible bacteria and in need of treatment. Other compounds of this invention may be similarly used.

What is claimed is:

1. A chemical compound of the formula:

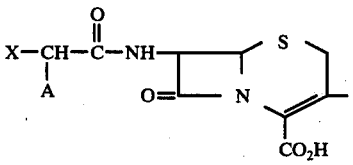

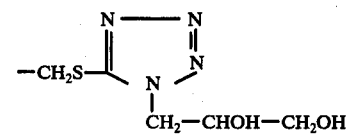

in which:
X is thienyl, furyl, phenyl or phenyl monosubstituted with hydroxy, hydroxymethyl, formamido or ureido; and
A is $NH_2$, OH, COOH, $SO_3H$, formyloxy or, when the α-C-hydrogen is absent, methoxyimino; and the nontoxic, pharmaceutically acceptable alkali metal salts of said chemical compound.

2. The compound of claim 1 being 7-D-mandelamido-3-[1-(2,3-dihydroxypropyl)tetrazole-5-ylthiomethyl]-3-cephem-4-carboxylic acid.

3. The compound of claim 1 being 7-D-α-aminophenylacetamido)-3-[1-(2,3-dihydroxypropyl)tetrazole-5-ylthiomethyl]-3-cephem-4-carboxylic acid.

4. The compound of claim 1 being 7-(d-α-p-hydroxyphenyl α-aminoacetamido)-3-[1-(2,3-dihydroxypropyl)-tetrazole-5-yl-thiomethyl]-3-cephem-4-carboxylic acid.

5. A antibacterial pharmaceutical composition comprising a compound as claimed in claim 1 and a pharmaceutically acceptable carrier therefor.

6. A method of treating bacterial infections comprising administering internally to an infected or susceptible human subject an antibacterially effective but nontoxic dose of a compound as claimed in claim 1.

* * * * *